United States Patent [19]

Ratcliff

[11] Patent Number: 4,793,989
[45] Date of Patent: * Dec. 27, 1988

[54] METHOD AND COMPOSITION FOR PREVENTION AND TREATMENT OF ORAL DISEASE

[76] Inventor: Perry A. Ratcliff, 7125 E. Lincoln Dr., Scottsdale, Ariz. 85253

[*] Notice: The portion of the term of this patent subsequent to Aug. 25, 2004 has been disclaimed.

[21] Appl. No.: 76,542

[22] Filed: Jul. 22, 1987

Related U.S. Application Data

[63] Continuation of Ser. No. 17,241, Dec. 29, 1986, Pat. No. 4,696,811, which is a continuation of Ser. No. 846,342, Mar. 31, 1986, abandoned, which is a continuation of Ser. No. 636,027, Jul. 30, 1984, abandoned, and a continuation of Ser. No. 947,079, Dec. 29, 1986, Pat. No. 4,689,215, which is a continuation of Ser. No. 846,342, Mar. 31, 1988, abandoned, which is a continuation of Ser. No. 636,027, Jul. 30, 1984, abandoned.

[51] Int. Cl.$^4$ ............................ A61K 33/20; A61K 7/20
[52] U.S. Cl. .................................... 424/53; 424/149
[58] Field of Search ............................ 424/53, 149

[56] References Cited

U.S. PATENT DOCUMENTS

| | | | |
|---|---|---|---|
| 2,451,897 | 10/1948 | Woodward | 99/111 |
| 2,482,958 | 9/1949 | Woodward | 99/150 |
| 2,546,258 | 3/1951 | Taylor | 99/150 |
| 2,711,363 | 6/1955 | Waihel | 23/85 |
| 2,871,097 | 1/1959 | Rapson | 23/152 |
| 3,084,995 | 4/1963 | Grubitsch | 23/152 |
| 3,147,124 | 9/1964 | Wentworth | 99/116 |
| 3,322,497 | 5/1967 | Martin | 23/152 |
| 3,585,147 | 6/1971 | Gordon | 252/187 |
| 3,591,515 | 7/1971 | Lovely et al. | 252/187 |
| 3,593,494 | 7/1971 | Durrell et al. | 23/154 |
| 3,754,079 | 8/1973 | Callerame | 423/472 |
| 3,828,097 | 8/1974 | Callerame | 23/72 |
| 4,104,190 | 8/1978 | Hartshorn | 252/187 |
| 4,247,531 | 1/1981 | Hicks | 423/477 |
| 4,250,144 | 2/1981 | Ratigan | 422/112 |
| 4,250,159 | 2/1981 | Cowley | 23/230 |
| 4,292,292 | 9/1981 | Hicks et al. | 423/477 |
| 4,330,531 | 5/1982 | Alliger | 424/53 |
| 4,362,707 | 12/1982 | Hardee et al. | 423/478 |
| 4,381,290 | 4/1983 | Hardee et al. | 423/478 |
| 4,396,592 | 8/1983 | Combroux | 423/478 |
| 4,414,193 | 11/1983 | Fredette et al. | 423/478 |
| 4,689,215 | 8/1987 | Ratcliff | 424/53 |
| 4,696,811 | 9/1987 | Ratcliff | 424/53 |

Primary Examiner—Shep K. Rose
Attorney, Agent, or Firm—Cahill, Sutton & Thomas

[57] ABSTRACT

The use of stabilized chlorine dioxide as a composition for the treatment and prevention of oral disease and the reduction of oral malodor is disclosed. Chlorine dioxide is an effective anti-plaque agent, anti-gingivitis and anti-periodontitis agent, and also effective to destroy malodorous sulfur compounds. Preferred concentrations are in the range of 0.005% to 2% and the chlorine dioxide may be in the form of a wash or rinse in solution, a soak or as a toothpaste.

6 Claims, No Drawings

METHOD AND COMPOSITION FOR PREVENTION AND TREATMENT OF ORAL DISEASE

This is a continuation of application Ser. No. 017,241, filed Dec. 29, 1986 (now U.S. Pat. No. 4,696,811) which is a continuation of application Ser. No. 846,342, filed Mar. 31, 1986 (now abandoned) which is a continuation of application Ser. No. 636,027, filed July 30, 1984 (now abandoned) and the present application is a continuation of application Ser. No. 947,079, filed Dec. 29, 1986 (now U.S. Pat. No. 4,689,215), which is a continuation of application Ser. No. 846,342, filed Mar. 31, 1986 (now abandoned) which is a continuation of application Ser. No. 636,027, filed July 30, 1984 (now abandoned); all of the above referenced prior applications name as inventor the same inventor as the present application.

The present invention relates to a method and composition for the prevention and treatment of oral disease and reduction of mouth odors. More particularly, the present invention relates to the use of stabilized chlorine dioxide for the prevention and treatment of oral disease and reduction of mouth odors.

The volatile sulfur compounds, hydrogen sulfide ($H_2S$) methylmercaptan ($CH_3SH$) and di-methylmercaptan ($CH_3)_2S$ are recognized in the current dental literature as being the major contributors or oral malodor. Numerous researchers using organoleptic, chemical, amperometric, mass spectrometric, or gas liquid chromatographic methods have demonstrated that these volatile sulfur compounds are present in the head space and vapor of putrified saliva and in individual samples of mouth air. In most persons, hydrogen sulfide and methylmercaptan constitute over 90% of the total volatile sulfur content identified in mouth air.

These malodorous volatile sulfur compounds are generated primarily through the putrifactive action of oral microorganisms on sulfur containing amino acids, peptones or proteins found in the mouth. These substrates are readily available in saliva and dental plaque or may be derived from proteinaceous food particles trapped between the teeth, in the gingival crevice or adhering to the mucous membranes and the irregular surface of the tongue as well as exfoliated oral epithelium, food debris and the like. Current studies have indicated that mouth odor not only comes from the posterior dorsal surface of the tongue but also from periodontal pockets. People with periodontal involvement have an attendant increase in oral malodor from disintegrated epithelial cells.

It is commonly accepted that the etiology of both smooth surface dental caries and periodontal disease is directly associated with the accumulation on teeth of bacterial plaque. Dental plaque is formed by a combination of events starting with a salivary proteanaceous coating of the tooth and the subsequent adhesion to the coating (pellicle) by streptococcus forms. Dextrans produced by bacteria, principally *S. mutans* and *S. sanguis*, are produced from sucrose and with the assistance of bacterially produced glucosyltransferases convert sucrose into glucose and fructose and ultimately the glucose into dextrans. The dextrans act as a nutrient substrate for the growth of additional organisms and the production of acids which demineralize both enamel and dentin causing decay. Other strains of alpha streptococci and lactobacillus organisms include but are not limited to *S. sanguis, S. mitis* and *S. salivarius*.

Gingivitis, adult and juvenile forms of periodontists and acute necrotizing uleratve gingivitis and other periodotopathies are known to be caused by bacteria. Gingivitis occurs from coronol dental plaque and periodontitis by the infection extending into the periodental pocket or space between the gingiva and the tooth root.

Various substances have been tested for their ability to disrupt plaque or prevent its formation and to treat mouth odor such as antibiotics, chlorhexdines, oxine, and alexidine.

The prior art compositions that have been used and tested have found some acceptance but are generally of limited efficacy in reducing or preventing dental caries and periodontitis, gingivitis, plaque accumulation and mouth malodor. Accordingly, there exists a clear need for a composition which will effectively inhibit or control the formation of bacterial plaque and suppress organisms such as but not limited to (1) *S. mutans,* which is implicated as the major cause of human dental decay; (2) *Bacteroides gingivalis,* an Actinobacillus Actinomycetumcomitans which is implicated in human periodontitis; and (3) will reduce odor intensity in the mouth through the control of hydrogen sulfide and methylmercaptan.

Broadly, the present invention contemplates the use of stabilized chlorine dioxide for the treatment of the mouth as a deodorizing agent, anti-plaque agent, bacteriacide for treatment of gingivitis and as a bactericidal fungicidal and viralcidal agent in other related applications. The term stabilized chlorine dioxide is a term well used in the industry and those skilled in the art will and do appreciate the various forms or compositions thereof which are available to perform certain intended functions and purposes. Furthermore, U.S. Pat. No. 3,271,242 describes a form of stabilized chlorine dioxide and a method of making same which is particularly useful in carrying out the present invention. Because the compound termed stabilized chlorine dioxide is well known to those skilled in the art, such knowledge permits the selection of a particular embodiment of such compound for specified purposes, as evidenced by pages 139 to 140 of a book entitled *Chlorine Dioxide* by W. J. Masschelein published by the Ann Arbor Science Publishers, Inc., copyright 1979; note also footnotes 112 to 116 cited therein which are: 112. Schirle, C. "Bull Inst. Text. Fr. 41: 21 (1953); 113. Haller, R. "Textil-Rundschau" 7: 359 (1952); 114. Das, D. B., and J. B. Speakman "J. Soc. Dyers Colurists" 66: 583 (1950); 115. German Pat. No. 1,027,629 (1958); "Chem, Abst." 54: 14712 (1960); 116. Tumanova, T. Z. "Bum. Prom." 6: 7 (1968); "Chem. Abstr." 69: 445522 (1968). A form of stabilized chlorine dioxide usable with the present invention is sold under the trademark "PUROGENE" by Oxyfresh USA, Inc. It is to be noted that Purogene may be purchased from any Service Center of the Sears department stores. Chlorine dioxide is quite soluble and is widely used as an industrial purification and oxidizing agent in such areas as manufacture of wood pulp, water treatment and similar applications due to its bactericidal, disinfectant, and sterilization qualities. In the present invention a composition containing stabilized chlorine dioxide may be used for treatment of the mouth either in a solution, for example, as a mouthwash or in a toothpaste generally in concentrations of below approximately 0.2% for the control of odorgenic microorganisms, bacterial plaque, gingivitis and bacteria which cause these conditions. Similarly, chlorine dioxide is also effective as a cellular debridement agent following surgical procedures, sanitizer denture soak and contact lens soaking agent.

The use of chlorine dioxide and its effects on man has been clinically evaluated. The relative safety of oral injestion of chlorine dioxide was demonstrated extensively in animals and later in humans by Lubbers, Chauan, and Bianchine, *Environmental Health Perspectives*, Volume 46, Pages 57–62, 1982.

EXAMPLE I

DEODORIZING MOUTHWASH

In an effort to find a suitable control agent for mouth odor, attention was directed towards the use of chlorine dioxide. The characteristics of chlorine dioxide which make it especially useful is that it is antiseptic, a bactericide, generally colorless, odorless, highly stable and has no apparent detrimental or deliterious effect on humans at concentrations involved. As pointed out above, mouth malodor is primarily caused by volatile sulfur compounds, hydrogen sulfide methylmercaptan and dimethyl mercaptan. These chemicals are produced as degradation products of microorganisms acting on exogenous and endogenous proteinaceous substrates, oral epithelium, food debris and saliva. In order to control mouth odor, a deodorizing mouth wash consisting of a solution of 0.02% chlorine dioxide in deionized water was utilized as a rinse. Evidence indicates efficacy at lesser dilutions to 0.005% with more rapid effect at dilutions of 0.2%. Sulfides are readily oxidized by chlorine dioxide. Bacteria implicated in the production of malodor were also effectively controlled. Inhibition of these microorganisms will reduce dental plaque.

The chlorine dioxide mouthwash or rinse solution serves to attack production and origin of malodor from the mouth by splitting the sulfide bonds of both hydrogen sulfide and methylmercaptan. Therefore, delivery of stabilized chlorine dioxide provides reduction and elimination of these odors. Further, the bacteriostatic, bactericidal, fungistatic and fungicidal activity of stabilized chlorine dioxide will reduce the number of microorganisms which assist in the production of oral debris leading to disintegration of organic compounds and ultimately producing hydrogen sulfide and methylmercaptan. The known organisms include staphlococci, *B. subtilis*, *B. pyrocaneus*, Colon bacilli, *B. melanogenicus*, Clostridia, *B. sporogenes*, *B. histolyticum*, and *T. mucosum*.

The mouthwash may be delivered as a simple rinse which bathes the tongue. Literature indicates that over 50% of mouth odor originates on the mouth and tongue surface, particularly the posterior dorsal surface of the tongue. Accordingly, a rinse is an effective treatment. However, persons with periodontal involvement may have an increase in oral malodor from disintegrated epithelial cells. A mouth rinse will not penetrate to attack gingival crevicular odorizers. Thus, to optimize treatment with a mouthwash containing chlorine dioxide, the wash must be delivered into the periodontal pockets as well as dorsal and lingual surfaces. To accomplish this, the preferred treatment is achieved by inserting the delivery tip of a syringe into the pockets or gingival crevices or by administering the wash by a mechanically powered water irrigating device such as those of the type sold under the trademark "Water Pik", manufactured by Teledyne Corp. Following irrigation, the user can swish the wash throughout the mouth, covering the dorsal surface of the tongue and other areas.

To improve the taste and appearance of the chlorine dioxide solution, appropriate sweeteners and colorings such as saccharin, peppermint and FTC #3 coloring agent may be added as is common with commercially available mouthwashes and is well-known to those in the art.

EVALUATION OF MOUTHWASH CONTAINING CHLORINE DIOXIDE FOR ITS EFFECT ON VOLATILE SULFUR COMPOUNDS

The test mouthwash which had a concentration of 0.05%, was dispersed in ⅜ oz. aliquots in individual plastic containers. The study was performed over a 3-hour period on six human subjects with objectionable early morning concentrations of volatile sulfur compounds (VSC) greater than 0.5 ng $CH_3SH$/10 ml mouth air.

Rinsing Procedure:

Following initial early morning VSC analysis on the day of evaluation, subjects were instructed to rinse, with vigorous swishing of rinse between teeth, for 30 seconds with ⅜ oz volumes of the test mouthwash. After the rinse was expectorated, the mouth was rinsed for 30 seconds with 15 ml of 18 megavolt pure water.

VSC Analysis:

All G.C. analysis were performed in duplicate on each subject at the following times:

1. Initial screening to select subjects with objectionable early morning concentrations of VSC.
2. On the day of evaluation, analysis were performed on early morning mouth air samples before rinsing. These values served as controls. Thus, each subject served as his own control against which the effect of the rinse was calculated. Immediately following these analysis, the subjects rinsed and were re-analyzed, 3 min., 13 min., one hour, two hours and 3 hours post-rinsing. The results are sumarized on the following table:

TABLE 8

| | | | | | | SUMMARY MOUTH AIR VSC REDUCTION | | | | | | | | |
|---|---|---|---|---|---|---|---|---|---|---|---|---|---|---|
| | Early Morning | | | One Hour | | | | Two Hour | | | | Three Hour | | |
| Subject | $H_2S$* | $CH_3SH$* | $H_2S$* | % Red | $CH_3SH$* | % Red | $H_2S$* | % Red | $CH_3SH$* | % Red | $H_2S$* | % Red | $CH_3SH$* | % Red |
| OF. 1 | 0.82 | 0.72 | 0.39 | 52.44 | 0.37 | 48.61 | 0.39 | 52.44 | 0.59 | 18.06 | 0.75 | 8.54 | 1.08 | +50 |
| OF. 2 | 1.30 | 1.04 | 0.29 | 77.69 | 0.17 | 83.65 | 0.41 | 68.46 | 0.24 | 76.92 | 0.45 | 65.38 | 0.23 | 72.88 |
| OF. 3 | 0.98 | 0.77 | 0.77 | 21.43 | 0.57 | 25.97 | 0.69 | 29.59 | 0.52 | 32.47 | 0.82 | 16.33 | 0.62 | 19.48 |
| OF. 4 | 0.73 | 1.04 | 0.39 | 46.58 | 0.2 | 75.00 | 0.37 | 49.32 | 0.31 | 70.19 | 0.47 | 35.62 | 0.46 | 55.76 |
| OF. 5 | 1.56 | 0.88 | 0.58 | 62.82 | 0.41 | 53.41 | 0.75 | 51.92 | 0.40 | 54.55 | 0.86 | 44.87 | 0.80 | 9.09 |
| OF. 6 | 1.12 | 1.41 | 0.40 | 64.29 | 0 | 100 | 0.41 | 63.39 | 0 | 100 | 0.55 | 50.89 | 0.43 | 69.50 |
| Average % Reduction | | | | 54.21 | | 64.44 | | 52.52 | | 58.70 | | 36.94 | | 30.25 |

*ng/10 ml volume of mouth air

The effectiveness of chlorine dioxide was tested both in vivo and in vitro and demonstrated that stabilized chlorine dioxide will kill at the 99% level in ten seconds streptococcus mutans the principle organism implicated in the etiology of dental caries as well as other strains of organisms as demonstrated by the following tests:

IN VITRO
THE BACTERICIDAL EFFECT OF $ClO_2$ AGAINST STREPTOCOCCUS MUTANS

| pH of Medium | 200 ppm $ClO_2$ | | SURVIVED | |
|---|---|---|---|---|
| | Treatment Seconds | Organisms/ 0.2 ml | No. Organisms | % Kill |
| 10 | 5 | 40,000 | 68 | 99.83 |
| | 10 | 40,000 | 16 | 99.96 |
| | 20 | 40,000 | 5 | 99.99 |
| 5 | 5 | 40,000 | 1336 | 99.66 |
| | 10 | 40,000 | 98 | 99.76 |
| | 20 | 40,000 | 101 | 99.75 |
| 1 | 5 | 29,600 | *TNTC | 0.0 |
| | 10 | 29,600 | 125 | 99.58 |
| | 20 | 29,600 | 70 | 99.76 |
| 6 | 5 | 29,600 | *TNTC | 0.0 |
| | 10 | 29,600 | *TNTC | 0.0 |
| | 20 | 29,600 | 122 | 99.59 |
| 6 | 5 | 9,400 | 744 | 92.1 |
| | 10 | 9,400 | 176 | 98.1 |
| | 20 | 9,400 | 44 | 99.5 |
| 2 | 5 | 9,400 | 1248 | 86.7 |
| | 10 | 9,400 | 920 | 90.2 |
| | 20 | 9,400 | 640 | 93.2 |

*Too numerous to count.

THE BACTERICIDAL EFFECT OF $ClO_2$ AGAINST BACTEROIDES GINGIVALIS

| pH of Medium | 200 ppm $ClO_2$ | | SURVIVED | |
|---|---|---|---|---|
| | Treatment Seconds | Organisms/ 0.2 ml | No. Organisms | % Kill |
| 5.21 | 5 | 53 | 0 | 100 |
| | 10 | 53 | 0 | 100 |
| | 20 | 53 | 0 | 100 |
| 5.96 | 5 | 53 | 0 | 100 |
| | 10 | 53 | 0 | 100 |
| | 20 | 53 | 0 | 100 |

THE BACTERICIDAL EFFECT OF $ClO_2$ AGAINST BACTEROIDES MELANINOGENICUS

| pH of Medium | 200 ppm $ClO_2$ | | SURVIVED | |
|---|---|---|---|---|
| | Treatment Seconds | Organisms/ 0.2 ml | No. Organisms | % Kill |
| 5.3 | 5 | 100,000 | 100,000 | 0 |
| | 10 | 100,000 | 100,000 | 0 |
| | 20 | 100,000 | 5,000 | 95 |
| 6.15 | 5 | 100,000 | 50,000 | 50 |
| | 10 | 100,000 | 50,000 | 50 |
| | 20 | 100,000 | 0 | 100 |
| 4.97 | 5 | 100,000 | 100,000 | 0 |
| | 10 | 100,000 | 100,000 | 0 |
| | 20 | 100,000 | 3,000 | 97 |
| 5.86 | 5 | 100,000 | 50,000 | 50 |
| | 10 | 100,000 | 50,000 | 50 |
| | 20 | 100,000 | 0 | 100 |
| 4.99 | 10 | 10,000 | 10,000 | 0 |
| | 20 | 10,000 | 0 | 100 |
| | 30 | 10,000 | 0 | 100 |
| 6.29 | 10 | 10,000 | 5,000 | 50 |
| | 20 | 10,000 | 0 | 100 |
| | 30 | 10,000 | 0 | 100 |
| 4.97 | 10 | 10,000 | 10,000 | 0 |
| | 20 | 10,000 | 0 | 100 |
| | 30 | 10,000 | 0 | 100 |
| 5.85 | 10 | 10,000 | 3,000 | 70 |
| 20 | 10,000 | 0 | 100 |
| 30 | 10,000 | 0 | 100 |

THE BACTERICIDAL EFFECT OF $ClO_2$ AGAINST ACTINOBACILLUS MYCETEMCOMITANS

| pH of Medium | 200 ppm $ClO_2$ | | SURVIVED | |
|---|---|---|---|---|
| | Treatment Seconds | Organisms/ 0.2 ml | No. Organisms | % Kill |
| 4.97 | 5 | 8,560 | *TNTC | 0 |
| | 10 | 8,560 | 312 | 96.3 |
| | 20 | 8,560 | 67 | 99.2 |
| 5.87 | 5 | 8,560 | *TNTC | 0 |
| | 10 | 8,560 | 2 | 99.9 |
| | 20 | 8,560 | 1 | 99.9 |

*Too numerous to count.

MATERIALS AND METHODS

Materials used in all experiments:
1.0 AC 5215 Odorid, $ClO_2$ 1000 ppm, Biocide Chemical Co. Norman, OK
1.1 Chlorine-free distilled water employed throughout
1.2 Stirring apparatus, magnetic mixer with magnetic bar; IEC Centrifuge 6000
1.3 Petri plates (12×50 mm, 15×100 mm)
1.4 HCl 0.1N, NaOH 0.1N
1.5 Sodium thiosulfate solution 15 1, employed 0.04 ml
1.6 Orthotolidine (o-toluidine) JT Baker, Baker Grade boiling point 200°–201° C. $C_4C_6H_4HN_2$, Standard Methods for Examination of Water and Wastewater, 14th Ed. 1975 Neutral Orthotolidine Reagent, 0.04 ml employed
1.7 Diluent, saline with 0.5% Tween 80

Materials used in individual experiments:
1.0 Exp. Streptococcus mutans ATCC #27152
1.1 Brain Heart Infusion Broth employed for initial culture
1.2 Plate counts performed on plate count agar.
2.0 Exp. Bacteroides gingivalis ATCC #33277
2.1 Anaerobic Typtic Soy Agar (TSA) with 5% sheep blood employed for initial isolation.
2.2 Plate counts were performed on anaerobic TSA with 5% horse serum
3.0 Exp. Bacteroides melaninogenicus ATCC #15930
3.1 Anaerobic TSA with 5% sheep blood was employed throughout
3.2 Extended time interval for stirring of organisms was 30 seconds
4.0 Exp. Actinobacillus actinomycetumocomitans ATCC #29522
4.1 Initial cultures prepared on chocolate agar
4.2 Plate counts were performed on anaerobic TSA without sheep blood

METHODS

Initially each ATCC culture employed was grown on the media documented under each organism. After isolation, all cultures were maintained on appropriate media. The initial bacterial count was determined by plating ten-fold serial dilutions of the selected organism in its respective medium. After incubation, the bacterial colonies were counted and 0.2 ml of the selected dilution was employed against $ClO_2$. $ClO_2$ was employed at 200 ppm. 0.8 ml of $ClO_2$ was mixed with 0.2 ml of organisms suspension and mag-mixed for the selected length of time in seconds—5, 10, 20, and 30. Two organism—$ClO_2$ mixtures were mixed by a 45° tilting rotation in a small tube for the selected period of time.

In each experiment, subsequent to each mixing time of $ClO_2$ organism-mixtures, excess $ClO_2$ was neutralized by the addition of 0.04 ml of sodium thiosulfate. To assure that complete neutralization of excess $ClO_2$ had occurred, 0.04 orthotolidine was added to each $ClO_2$—organism-sodium thiosulfate mixture. When $ClO_2$ is neutralized, the mixture remains clear. If residual $ClO_2$ is present, the mixture turns yellow after the addition of orthotolidine. Additional controls to determine the effect of each reagent singly or in combination against each organism include sodium thiosulfate-organism mixtures and sodium thiosulfate orthotolidine organism mixtures. A control plate count without reagents was included for each organism.

All cultures except *Streptococcus mutans* were grown anaerobically in CO at 37° C. for 48-96 hours. *Streptococcus mutans* was grown aerobically at 37° C. for 48 hours.

IN VIVO
CHLORINE DIOXIDE EVALUATION

Thirty-nine periodontal pockets in twenty-nine patients were examined by dark field and phase microscopy. The motility and density of bacteria were evaluated from zero to three with zero being no activity and three very active.

Of the thirty-nine teeth, thirty were molars, three were bicuspids and six were in the anterior region. Pocket dept ranged from 4 to 12 millimeters.

The patients were instructed to use a 0.1% chlorine dioxide solution twice daily. Four of the patients used chlorine dioxide as a mouth rinse and twenty-five used it as an irrigant with monoject 412 twelve cc syringe.

The findings follow:

| CLINICAL EFFECT OF .1% CHLORINE DIOXIDE | | | | | | | | |
|---|---|---|---|---|---|---|---|---|
| TOOTH # | CODE # | SURFACE | BEFORE PHASE | AFTER PHASE | % CHANGE | BEFORE DARK FIELD | BEFORE DARK FIELD | % CHANGE |
| 14 | 001 | M | 2 | 0 | 100% | 3 | 1+ | 50% |
| 23 | 001 | D | + | 0 | 100% | 2 | + | 75% |
| 30 | 002 | D | 0 | 0 | 0% | 1 | 0 | 100% |
| 18 | 003 | D | 2 | 0 | 100% | 2+ | 1− | 70% |
| 15 | 004 | L | + | 0 | 100% | + | + | 0% |
| 18 | 004 | D | 2 | 0 | 100% | 2+ | 1 | 60% |
| 14 | 005 | M | 2 | 1 | 50% | 2 | 2 | 0% |
| 30 | 005 | L | 1 | 0 | 100% | 2 | 0 | 100% |
| 15 | 006 | L | 0 | 0 | 0 | 2 | 0 | 100% |
| 19 | 007 | D | 0 | 0 | 0 | 3 | 0 | 100% |
| 31 | 008 | B | 2 | 0 | 100% | 2+ | 0 | 100% |
| 7 | 009 | D | 3 | 0 | 100% | 3 | 2 | 33% |
| 2 | 010 | M | 1 | 0 | 100% | 2 | 0 | 100% |
| 4 | 011 | M | 0 | 0 | 0 | 2 | 0 | 100% |
| 15 | 011 | D | 1 | 0 | 100% | 3 | 1− | 75% |
| 3 | 012 | M | 2 | 1− | 63% | 3 | 2 | 33% |
| 14 | 012 | M | 2 | 1 | 50% | 3 | 2 | 33% |
| 18 | 013 | M | 0 | 0 | 0 | 3 | 1 | 67% |
| 3 | 014 | M | 0 | 0 | 0 | 1 | 0 | 100% |
| 2 | 015 | M | 2 | 1 | 50% | 3 | 2 | 33% |
| 2 | 015 | D | 2 | + | 75% | 3 | + | 83% |
| 21 | 016 | D | 0 | 0 | 0 | 2+ | 0 | 100% |
| 14 | 017 | M | 1 | 0 | 100% | 3 | 2 | 33% |
| 3 | 018 | M | 1 | 0 | 100% | 1 | 0 | 100% |
| 32 | 019 | D | 1+ | 0 | 100% | 2 | 0 | 100% |
| 31 | 020 | B | 2 | + | 75% | 3 | + | 83% |
| 2 | 021 | M | 2+ | 1 | 60% | 3 | 2 | 33% |
| 32 | 022 | D | 1 | 0 | 100% | 1 | + | 50% |
| 31 | 023 | M | 1 | 0 | 100% | 3 | 0 | 100% |
| 3 | 024 | D | 2 | 0 | 100% | 2 | 0 | 100% |
| 15 | 025 | D | 2 | 0 | 100% | 3 | 1 | 67% |
| 26 | 025 | D | 0 | 0 | 0 | 3 | 1 | 67% |
| 4 | 026 | M | 2 | 0 | 100% | 2+ | 1− | 70% |
| 12 | 026 | M | 1 | + | 50% | 3 | + | 83% |
| 8 | 027 | B | 1 | 0 | 100% | 2 | 1 | 50% |
| 3 | 028 | M | 1 | 0 | 100% | 3 | 1 | 67% |
| 31 | 029 | M | 1 | + | 50% | 3 | 1+ | 50% |
| 11 | 030 | D | + | 0 | 100+ | 1 | + | 50% |

| EVALUATION DATA | | |
|---|---|---|
| Number of Pockets | % Resolution | % of Total |
| Phase | | |
| (Thirty Pockets with Activity) | | |
| 21 | 100% | 70% |
| 2 | 75% | 6.67% |
| 1 | 63% | 3.33% |
| 1 | 60% | 3.33% |
| 5 | 50% | 16.07% |
| Mean resolution | | |
| (All bacterial activity stopped or was reduced). | | |
| Dark Field | | |
| (Thirty-nine pockets with Activity) | | |

-continued

| EVALUATION DATA | | |
|---|---|---|
| Number of Pockets | % Resolution | % of Total |
| 14 | 100% | 35.89% |
| 3 | 83% | 7.69% |
| 2 | 75% | 5.13% |
| 2 | 70% | 5.13% |
| 4 | 67% | 10.26% |
| 1 | 60% | 2.56% |
| 5 | 50% | 12.82% |
| 6 | 33% | 15.38% |

(Two of the pockets exhibited no reduction in bacteria after the use of Chlorine Dioxide.)

EXAMPLE II

TOOTHPASTE

As demonstrated above, chlorine dioxide can be an effective agent on odor producing microorganisms and enzymes. However, the effectiveness of chlorine dioxide can be enhanced when included as an ingredient of a toothpaste. Toothpaste is more effective than a rinse for removing malodor from the gums or gingiva. The action of the brush dislodges dead cells and putrescent debris from the gingival crevices as well as on the various mouth surfaces and on the tongue. The chlorine dioxide contained in the toothpaste acts as discussed above to prevent malodor and serve as a deodorizer by attacking hydrogen sulfide and methylmercaptan. A typical toothpaste would have the following composition: Chlorine dioxide approximately 0.005% to 0.2%, detergent polishing agent; calcium carbonate; flavoring, saccharin; peppermint; coloring agent. These other ingredients may vary and are the basic ingredients in many toothpastes as is well-known to those in the art. Other formulations including chlorine dioxide as the active incredient would work as well.

EXAMPLE III

ANTI-PLAQUE AGENT

Dental plaque, as mentioned above, is formed by a combination of actions beginning with saliva coating the the tooth and a subsequent adhesion to the coating by streptococcus bacterial forms. *S. mutans* degrade sucrose into glucose or fructose which are then compounded into dextrans and levans. The dextrans act as a nutrient substrate for the growth of additional organisms and the production of acids which demineralize tooth enamel and dentin causing tooth decay. As indicated in the test data above, chlorine dioxide is lethal to streptococcus mutans in vitro and materally reduces their numbers in vivo. Dental plaque formation is reduced when the microbial content of the mouth is reduced. Thus, chlorine dioxide is an effective anitmicrobial agent which functions as a dental plaque retardant or preventative and as an anti-cariogenic agent. Preferred concentrations are in the range from 0.005% to 0.2% in solutions as for example, in de-ionized water with suitable coloring and flavorings for patient comfort.

EXAMPLE IV

ANTI-GINGIVITIS, ANTI-PERIODONTITIS AND GINGIVAL BLEEDING PREVENTATIVE

Gingivitis and the various forms of periodontitis are known to be caused by bacteria. Principal forms implicated are bacteroides Gingivalis and *Actinobacillus actionmycetumcomitans*. Gingivitis occurs from coronal dental plaque and periodontitis by the infection extending into the periodontal pockets or spaced between the gingiva (gums) and the tooth root. Thus control of gingivitis is by reduction of microorganisms in the coronal dental plaque and control of periodontitis by reduction of pocket bacterial plaque in the gingival crevices as well as the saliva.

Clinical evidence has documented improvement in treatment of the above diseases when stabilized chlorine dioxide is used. The organisms currently implicated in the above are listed as follows:

1. Gingivitis

Actinomyces forms including Actinomyces Israeli
Coccus forms

2. Acute Necrotizing Ulcerative Gingivitis

Spirochetes
Bacteroides Intermedius
Fusiform Nucleatum

3. Juvenile Periodontitis

Actinobacillus Actinomycetumcomitans
Capnocytophagia
Bacteroides Intermedius

4. Adult periodontitis

Bacteroides Gingivalis
Bacteroides Intermidius
Actinobacillus Actinomycetumcomitans
Vibrio Nucleatum
Fusobactium Nucleatum
Fusobactium Bacteroides
Anerobic Cocci Research has demonstrated that stabilized chlorine dioxide is lethal to *Bacteriodes gingivalis* and Actincbacillus Actinomycetumcomitans in vitro at the 95% level in twenty seconds with a 0.02% concentration. Research in vivo demonstrates that these organisms are significantly reduced or eliminated in humans when chlorine dioxide agent is applied to the pocket area using a syringe or water injection device with a needle to force penetration into the gingival crevices with the chlorine dioxide concentration in the range of 0.05% to 0.2%. Both gingivitis and periodontitis cause an increase in the rate of epithelial cells sloughing aggrevating oral malodor and causing some ulceration of tissue leaving the gingival bleeding which is also reduced by reatment with a solution of stabilized chlorine dioxide.

Chlorine dioxide is thus highly useful in the treatment of gingivitis, periodontitis in its various forms and bleeding gingiva.

EXAMPLE V

DENTURE SOAK

The malodors of the mouth result substantially from the volatile sulfur compounds which are present in saliva. Saliva coats and penetrates dental prosthetic devices including full dentures and partial dentures. Further, food and other cellular debris adheres to dental prostheses. Bacteria accumulates on and in the microscopic faults and pores of these prosthetic devices. Chlorine dioxide has been demonstrated as a bactericide and disinfectant and is effective for neutralizing sulfur-based malodors, removing organic debris from dental prosthesis and as a disinfectant and bactericide. As a dental soak the solution is antimicrobial, removes sulfur compounds and breaks down organic material and can be used in solution form having a concentration of from approximately 0.002% to 0.27%.

EXAMPLE VI

CELLULAR DEBRIDEMENT AGENT

Many wounds and desquamative diseases such as Lichen Planus, Desquamative Gingivitis and desquamative dermatological disease are aided by organic debridement agents and antimicrobial agents. Solution or composition containing chlorine dioxide in 0.05% to 0.1% and higher concentrations is effective to treat these problems. One particular application would be in veterinarian applications for the purpose of reducing odor attendant to these wounds and diseases.

EXAMPLE VII

SANITIZER AND COLD STERILIZATION AGENT

The known bacterial, fungicidal and viralcidal characteristics of chlorine dioxide also make it extremely useful as a sanitizer which can be a solution in which materials can be dipped or by application in an areosol spray. The sanitizer can be used for food, sickroom use, bathroom and cold sterilization of many instruments and pieces of equipment are generally not amenable to autoclave sterilization. Again, the concentration of the sanitizing or sterilization agent would preferably be in the range of from 0.005% to 2.0%.

EXAMPLE VIII

CONTACT LENS SOAK

Contact lenses accumulate bacteria and cellular debris from the eye. The known bactericidal, fungicidal and viraloidal capacity of chlorine dioxide along with the low toxicity makes chlorine dioxide solution an ideal lens soak. In addition, capacity to degrade organic debris keeps the lens clean and nonirritating. The preferred range of concentration is 0.005% to 0.2% in sterilized water.

It will be seen from the foregoing that chlorine dioxide in solution or as part of a composition or compound is effective in treating and preventing the formation of mouth malodor, as a suitable chemical plaque control agent, and as a bactericide, viralcide and fungicide superior to other compositions used today. Chlorine dioxide has been used for many years in other areas and extensive study in animals and in man have demonstrated its low toxicity and safety. Chlorine dioxide is approved by the Environmental Protection Agency (EPA Reg. No. 9048-3) for water purification, food preparation and preservation as well as a bacteriostatic, fungistatic and viralstatic agent.

It will be obvious that various changes, alterations and modifications to the method and process described herein may be made. To the extent that such changes, alterations and modifications do not depart from the spirit and scope of the appended claims, they are intended to be emcompassed therein.

I claim:

1. A method for cleaning a dental prosthetic device, said method comprising the step of irrigating the dental prosthetic device with a solution containing stabilized chlorine dioxide in a concentration in the range of 0.002% to 0.27%.

2. The method as set forth in claim 1 wherein the concentration of the solution of stabilized chlorine dioxide is in the range of 0.005% to 0.2%.

3. The method as set forth in claim 1 including the step or soaking the dental prosthetic device in a solution of stabilized chlorine dioxide and at a location outside of the oral cavity.

4. A method for reducing the degradation of proteins associated with a dental prosthetic into hydrogen sulphide and methylmercaptan, said method comprising the step of reducing the motility and mitosis of all oral bacteria through irrigation of the dental prosthetic at a location outside of the oral cavity with a solution containing stabilized chlorine dioxide in a concentration in the range of 0.002% to 0.27%.

5. The method as set forth in claim 4 wherein the oral bacteria include *Bacteroides melaninogenicus*.

6. The method as set forth in claim 4 wherein the concentration of stabilized chlorine dioxide is in the range of 0.005% to 0.2%.

* * * * *

UNITED STATES PATENT AND TRADEMARK OFFICE
CERTIFICATE OF CORRECTION

PATENT NO. : 4,793,989

DATED : December 27, 1988

INVENTOR(S) : Perry A. Ratcliff

Page 1 of 4

It is certified that error appears in the above-identified patent and that said Letters Patent is hereby corrected as shown below:

Column 5, lines 8-30 should be deleted to appear as shown below.

IN VITRO

THE BACTERICIDAL EFFECT OF $ClO_2$ AGAINST STREPTOCOCCUS MUTANS

| pH of Medium | Treatment Seconds | 200 ppm $ClO_2$ Organisms/0.2ml | SURVIVED No. Organisms | % Kill |
|---|---|---|---|---|
| 4.80 | 5  | 40,000 | 68   | 99.83 |
|      | 10 | 40,000 | 16   | 99.96 |
|      | 20 | 40,000 | 5    | 99.99 |
| 5.95 | 5  | 40,000 | 1336 | 99.66 |
|      | 10 | 40,000 | 98   | 99.76 |
|      | 20 | 40,000 | 101  | 99.75 |
| 5.01 | 5  | 29,600 | *TNTC | 0.0  |
|      | 10 | 29,600 | 125  | 99.58 |
|      | 20 | 29,600 | 70   | 99.76 |
| 6.06 | 5  | 29,600 | *TNTC | 0.0  |
|      | 10 | 29,600 | *TNTC | 0.0  |
|      | 20 | 29,600 | 122  | 99.59 |
| 5.06 | 5  | 9,400  | 744  | 92.10 |
|      | 10 | 9,400  | 176  | 98.10 |
|      | 20 | 9,400  | 44   | 99.50 |
| 6.02 | 5  | 9,400  | 1248 | 86.7  |
|      | 10 | 9,400  | 920  | 90.2  |
|      | 20 | 9,400  | 640  | 93.2  |

* Too numerous to count

UNITED STATES PATENT AND TRADEMARK OFFICE
CERTIFICATE OF CORRECTION

PATENT NO. : 4,793,989

DATED : December 27, 1988

INVENTOR(S) : Perry A. Ratcliff

Page 2 of 4

It is certified that error appears in the above-identified patent and that said Letters Patent is hereby corrected as shown below:

Column 5, lines 45-68 should be deleted to appear as shown below.

THE BACTERICIDAL EFFECT OF $ClO_2$ AGAINST BACTEROIDES MELANINOGENICUS

| pH of Medium | Treatment Seconds | 200 ppm $ClO_2$ Organisms/0.2ml | SURVIVED No. Organisms | % Kill |
|---|---|---|---|---|
|       | 5  | 100,000 | 100,000 | 0   |
| 5.3   | 10 | 100,000 | 100,000 | 0   |
|       | 20 | 100,000 | 5,000   | 95  |
|       | 5  | 100,000 | 50,000  | 50  |
| 6.15  | 10 | 100,000 | 50,000  | 50  |
|       | 20 | 100,000 | 0       | 100 |
|       | 5  | 100,000 | 100,000 | 0   |
| 4.97  | 10 | 100,000 | 100,000 | 0   |
|       | 20 | 100,000 | 3,000   | 97  |
|       | 5  | 100,000 | 50,000  | 50  |
| 5.86  | 10 | 100,000 | 50,000  | 50  |
|       | 20 | 100,000 | 0       | 100 |
|       | 10 | 10,000  | 10,000  | 0   |
| 4.99  | 20 | 10,000  | 0       | 100 |
|       | 30 | 10,000  | 0       | 100 |
|       | 10 | 10,000  | 5,000   | 50  |
| 6.29  | 20 | 10,000  | 0       | 100 |
|       | 30 | 10,000  | 0       | 100 |
|       | 10 | 10,000  | 10,000  | 0   |
| 4.97  | 20 | 10,000  | 0       | 100 |
|       | 30 | 10,000  | 0       | 100 |
|       | 10 | 10,000  | 3,000   | 70  |
| 5.85  | 20 | 10,000  | 0       | 100 |
|       | 30 | 10,000  | 0       | 100 |

UNITED STATES PATENT AND TRADEMARK OFFICE
CERTIFICATE OF CORRECTION

PATENT NO. : 4,793,989

DATED : December 27, 1988

INVENTOR(S) : Perry A. Ratcliff

It is certified that error appears in the above-identified patent and that said Letters Patent is hereby corrected as shown below:

Column 7 and 8 under tooth after "32" last occurrence delete the remainder of the Table and substitute as shown below.

CLINICAL EFFECT OF .1% CHLORINE DIOXIDE

| TOOTH # | CODE # | SUR-FACE | BEFORE PHASE | AFTER PHASE | % CHANGE | BEFORE DARK FIELD | BEFORE DARK FIELD | % CHANGE |
|---|---|---|---|---|---|---|---|---|
| 31 | 023 | M | 1 | 0 | 100% | 3 | 0 | 100% |
| 3 | 024 | D | 2 | 0 | 100% | 2 | 0 | 100% |
| 15 | 025 | D | 2 | 0 | 100% | 3 | 1 | 67% |
| 26 | 025 | D | 0 | 0 | 0 | 3 | 1 | 67% |
| 4 | 026 | M | 2 | 0 | 100% | 2+ | 1- | 70% |
| 12 | 026 | M | 1 | + | 50% | 3 | + | 83% |
| 8 | 027 | B | 1 | 0 | 100% | 2 | 1 | 50% |
| 3 | 028 | M | 1 | 0 | 100% | 3 | 1 | 67% |
| 31 | 029 | M | 1 | + | 50% | 3 | 1+ | 50% |
| 11 | 030 | D | + | 0 | 100% | 1 | + | 50% |

UNITED STATES PATENT AND TRADEMARK OFFICE
CERTIFICATE OF CORRECTION

PATENT NO. : 4,793,989

DATED : December 27, 1988

INVENTOR(S) : Perry A. Ratcliff

It is certified that error appears in the above-identified patent and that said Letters Patent is hereby corrected as shown below:

Column 4, line 26, "0.05%," should read --0.5%--.

Signed and Sealed this

Eighth Day of August, 1989

Attest:

DONALD J. QUIGG

*Attesting Officer*  *Commissioner of Patents and Trademarks*

UNITED STATES PATENT AND TRADEMARK OFFICE
CERTIFICATE OF CORRECTION

PATENT NO. : 4,793,989
DATED : Dec. 27, 1988
INVENTOR(S) : Perry A. Ratcliff

It is certified that error appears in the above-identified patent and that said Letters Patent is hereby corrected as shown below:

On the title page, the data in item [63] Related U.S. Application Data, should be deleted and substitute therefor:

--Continuation of Ser No. 017,241, Dec. 29, 1986, Pat. No. 4,696,811, which is a continuation of Ser. No. 846,342, Mar. 31, 1986, abandoned, which is a continuation of Ser. No. 636,027, Jul. 30, 1984, abandoned.--

Column 1, delete lines 6-16, and substitute therefor:

--This is a continuation of application Ser. No. 017,241, filed Dec. 29, 1986 (now U.S. Pat. No. 4,696,811) which is a continuation of application Ser. No. 846,342, filed Mar. 31, 1986 (now abandoned) which is a continuation of application Ser. No. 636,027, filed Jul. 30, 1984 (now abandoned).--

Signed and Sealed this

Third Day of November, 1998

Attest:

BRUCE LEHMAN

Attesting Officer

Commissioner of Patents and Trademarks